(12) United States Patent
Dolnik

(10) Patent No.: US 10,564,121 B2
(45) Date of Patent: Feb. 18, 2020

(54) DEVICE AND METHOD FOR SEPARATION AND ANALYSIS OF TRACE AND ULTRA-TRACE IONOGENIC COMPOUNDS BY ISOTACHOPHORESIS AND ZONE ELECTROPHORESIS ON CHIP

(71) Applicant: Vladislav Dolnik, Palo Alto, CA (US)

(72) Inventor: Vladislav Dolnik, Palo Alto, CA (US)

( * ) Notice: Subject to any disclaimer, the term of this patent is extended or adjusted under 35 U.S.C. 154(b) by 120 days.

(21) Appl. No.: 14/952,930

(22) Filed: Nov. 26, 2015

(65) Prior Publication Data
US 2017/0153202 A1    Jun. 1, 2017

(51) Int. Cl.
*G01N 27/447*    (2006.01)

(52) U.S. Cl.
CPC . *G01N 27/44791* (2013.01); *G01N 27/44743* (2013.01); *G01N 27/44773* (2013.01)

(58) Field of Classification Search
CPC ....... G01N 27/44791; G01N 27/44743; G01N 27/44773; G01N 27/447
See application file for complete search history.

(56) References Cited

U.S. PATENT DOCUMENTS

| | | | |
|---|---|---|---|
| 6,803,019 B1 * | 10/2004 | Bjornson | G01N 27/44791 422/504 |
| 7,691,245 B2 * | 4/2010 | Manz | C07K 1/26 204/453 |
| 7,799,195 B2 | 9/2010 | Dolnik | |
| 9,228,977 B2 | 1/2016 | Mahabadi | |
| 2003/0150733 A1 * | 8/2003 | Ramsey | B01F 13/0062 204/600 |
| 2005/0109621 A1 | 5/2005 | Hauser | |
| 2011/0120867 A1 * | 5/2011 | Mishina | G01N 27/44743 204/451 |
| 2016/0084805 A1 * | 3/2016 | Kelly | G01N 30/08 204/451 |

FOREIGN PATENT DOCUMENTS

CZ    246727    4/1986

OTHER PUBLICATIONS

Hauser et al. "High-Voltage Capacitively Coupled Contactless Conductivity Detection for Microchip Capillary Electrophoresis" Anal. Chem. 2002, 74, 6378-6382 (Year: 2002).*

(Continued)

*Primary Examiner* — Susan D Leong (57) ABSTRACT

Disclosed herein is a device for separation and analysis of trace and ultra-trace ionogenic compounds by isotachophoresis-zone electrophoresis on a chip with online detection and method of its use, concentrating trace and ultra-trace analytes by isotachophoretic migration in a wide separation channel when a manifold of auxiliary electrodes is employed. Then the isotachophoretic zones of trace and ultra-trace analytes are transferred by isotachophoretic migration through a tapered channel, while corresponding auxiliary electrodes are progressively disconnected from the power supply. When the isotachophoretic zones enter the analytical capillary channel, the mode switches to zone electrophoresis and an online detector detects analytes for qualitative and quantitative analysis.

21 Claims, 3 Drawing Sheets

(56) References Cited

OTHER PUBLICATIONS

P. Bocek, M. Deml, B. Kaplanova, J. Janak, Analytical isotachophoresis: The concept of the separation capacity. J. Chromatogr., 1979, 160, 1-9.

R. Bodor, M. Žuborova, E. Ôlvecka, V. Madajova, M. Masar, D. Kaniansky, B. Stanislawski, Isotachophoresis and isotachophoresis-zone electrophoresis of food additives on as chip with column-coupling separation channels. J. Sep. Sci, 2001, 24, 802-809.

M. Deml, P. Bocek, J. Janak : High-speed isotachophoresis: current supply and detection system. J. Chromatogr. A, 109, 1975, 49-55.

V. Dolnik, M. Deml, P. Bocek, Large sample volume preseparation for trace analysis in isotachophoresis. J Chromatogr, 1985, 320, 89-97.

V. Dolnik, M. Deml, P. Bocek, Determination of oxalate in human serum by multicolumn isotachophoresis. Electrophoresis, 1988, 9,:839-841.

V. Dolnik, M. Deml, P. Gebauer, P. Bocek, Optimization of isotachophoretic analysis: use of the charge-based transient state model. J. Chromatogr., 1991, 545, 249-266.

F. M. Everaerts, Th.P.E.M. Verheggen, F. E.P. Mikkers, Determination of substances at low concentrations in complex mixtures by isotachophoresis with column coupling. J. Chromatogr. A, 1979, 169, 21-38.

X. C. Huang , M. A. Quesada , R. A. Mathies: Capillary array electrophoresis using laser-excited confocal fluorescence detection. Anal. Chem., 1992, 64, 967-972.

D. Kaniansky, M. Masar, J. Bielcikova, F. Ivanyi, F. Eisenbeiss, B. Stanislawski, B. Grass, A. Neyer, M. Johnck, Capillary electrophoresis separations on a planar chip with the column-coupling configuration of the separation channels. Anal Chem. 2000, 72, 3596-3604.

J. Tanyanyiwa and P. C. Hauser: High-voltage contactless conductivity detection of metal ions in capillary electrophoresis. Electrophoresis, 2002, 23, 3781-3786.

Stephen C. Jacobson, Roland Hergenroder, Lance B. Koutny, R. J. Warmack, and J. Michael Ramsey: Effects of Injection Schemes and Column Geometry on the Performance of Microchip Electrophoresis Devices. Anal. Chem., 1994, 66 (7), pp. 1107-1113.

P. Kuban and P. C. Hauser: A review of the recent achievements in capacitively coupled contactless conductivity detection. Anal. Chim. Acta, 607, 2008, 15-29.

P. Kuban and P. C. Hauser: 20th anniversary of axial capacitively coupled contactless conductivity detection in capillary electrophoresis. TrAC Trends in Analytical Chemistry, 2018, 102, 311.

L.D. Thredgold, D. A. Khodakov, A. V. Ellis and C, E. Lenehan; On-chip capacitively coupled contactless aonductivity detection using "injected" metal electrodes. Analyst, 2013, 138, 4275.

P. Kuban and P. C. Hauser: Evaluation of microchip capillary electrophoresis with external contactless conductivity detection for the determination of major inorganic ions and lithium in serum and urine samples. Lab Chip, 2008, 8, 1829.

M.T. Ackermans, F.M. Everaerts, J.L. Beckers : Determination of aminoglycoside antibiotics in pharmaceuticals by capillary zone electrophoresis with indirect UV detection coupled with micellar electrokinetic capillary chromatography. J. Chromatogr. A, 1992, 606, 228-235.

G. A. Blanco, Y. H. Nai, E. F. Hilder, R. A. Shellie, G. W. Dicinoski, P. R. Haddad, M. C. Breadmore: identification of inorganic improvised explosive devices using sequential injection capillary electrophoresis and contactless conductivity detection. Anal. Chem., 2011, 83, 9068-9075.

P. Bocek, M. Deml, P. Gebauer and V. Dolnik: Analytical Isotachophoresis. VCH Verlagsgesellschaft, Weinheim—New York, 1988.

J. A. Fracassi da Silva and C. L. do Lago : An Oscillometric Detector for Capillary Electrophoresis. Anal. Chem., 1998, 70, 4339-4343.

P. Gebauer, V. Dolnik, M. Deml and P. Bocek: Recent trends in capillary isotachophoresis. Adv. Electrophoresis, 1987, 1, 281-359.

H. T. Feng, H.-P. Wei, S. F. Y. Li: On-chip potential gradient detection with a portable capillary electrophoresis system. Electrophoresis 2004, 25, 909-913.

E. M. Abad-Villar, J. Tanyanyiwa, M. T, Fernandez-Abdul, A. Costa-Garcia, and P. C. Hauser, Detection of Human Immunoglobulin in Microchip and Conventional Capillary Electrophoresis with Contactless Conductivity Measurements. Anal. Chem. 2004, 76, 1282-1288.

M. Galloway, W. Stryjewski, A. Henry, S. M. Ford, S. Llopis, R. L. McCarley and S. A. Soper: Contact Conductivity Detection in Poly(methyl methacylate)-Based Microfluidic Devices for Analysis of Mono- and Polyanionic Molecules. Anal. Chem. 2002, 74, 2407-2415.

H. Shadpour, M. L. Hupert, D. Patterson, C. Liu, M. Galloway, W. Stryjewski, J. Goettert, and S. A. Soper: Multichannel Microchip Electrophoresis Device Fabricated in Polycarbonate with an Integrated Contact Conductivity Sensor Array. Anal. Chem. 2007, 79, 870-878.

F. Laugere, R. M. Guijt, J. Bastemeijer, G. van der Steen, A. Berthold, E. Baltussen, P. Sarro, G. W. K. van Dedem, M. Vellekoop, and A. Bosshe: On-Chip Contactless Four-Electrode Conductivity Detection for Capillary Electrophoresis Devices. Anal. Chem. 2003, 75, 306-312.

X. Huang, T.-K. J. Pang, M. J. Gordon, and R. N. Zare: On-Column Conductivity Detector for Capillary Zone Electrophoresis. Anal. Chem. 1997, 59, 2747-2749.

P. Kuban and P. C. Hauser: Application of an external contactless conductivity detector for the analysis of beverages by microchip capillary electrophoresis. Electrophoresis 2005, 26, 3169-3178.

Z. Liang, N. Chiem, G. Ocvirk, T. Tang, K. Fluri, and D. J. Harrison: Miccrofabrication of a Planar Absorbance and Fluorescence Cell for Integrated Capillary Electrophoresis Devices. Anal. Chem. 1996, 68, 1040-1046.

Shi, Y., Simpson, P., Scherer, J. R., Wexler, D., Skibola, C., Smith, M. T. and Mathies, R. A. Radial Capillary Array Electrophoresis Microplate and Scanner for High-Performance Nucleic Acid Analysis, Analytical Chemistry 71, 5354-5361 (1999).

S. Pasas, B. Fogarty, B. Huynh, N. Lacher, B. Carlson, S. Martin, W. Vandaveer, S. Lunte, "Separation Methods Microanalytical Systems", in Detection on Microchips: principles, challenges, hyphenation and integration, Jörg P. Kutter and Yolanda Fintschenko (Editors), CRC Press, (2006), 433-497.

* cited by examiner

DEVICE AND METHOD FOR SEPARATION AND ANALYSIS OF TRACE AND ULTRA-TRACE IONOGENIC COMPOUNDS BY ISOTACHOPHORESIS AND ZONE ELECTROPHORESIS ON CHIP

STATEMENT REGARDING FEDERALLY SPONSORED RESEARCH

The patent application is based on research sponsored by NIH SBIR grant number 1 R43ES022366-01.

REFERENCES CITED

U.S. Patent Documentation

U.S. Pat. No. 5,074,982 Suppression of electroosmosis with hydrolytically stable coatings.

U.S. Pat. No. 5,567,292 Polymers for separation of biomolecules by capillary electrophoresis U.S. Pat. No. 6,410,668 Robust polymer coating U.S. Pat. No. 7,799,195 Neutral polysaccharide wall coating for electrophoretic and chromatographic separations in capillaries and microchannels

Other References

M. T. Ackermans, F. M. Everaerts, J. L. Beckers: *Determination of aminoglycoside antibiotics in pharmaceuticals by capillary zone electrophoresis with indirect UV detection coupled with micellar electrokinetic capillary chromatography*. J. Chromatogr. A, 1992, 606, 228-235.

G. A. Blanco, Y. H. Nai, E. F. Hilder, R. A. Shellie, G. W. Dicinoski, P. R. Haddad, M. C. Breadmore, *Identification of inorganic improvised explosive devices using sequential injection capillary electrophoresis and contacless conductivity detection*. Anal. Chem., 2011, 83, 9068-9075.

P. Boček, M. Deml, B. Kaplanová, J. Janák, *Analytical isotachophoresis: The concept of the separation capacity*. J. Chromatogr., 1979, 160, 1-9.

P. Boček, M. Deml, J. Janák, *Effect of a concentration cascade of the leading electrolyte on the seperation capacity in isotachophoresis*. J. Chromatogr., 1978, 156, 323-326.

P. Boček, I. Medziak, M, Deml, J, Janák, *Use of complex formation equilibria in the analytical isotachophoresis of strong electrolyte ions: Separation of halides and sulphates*. J. Chromatogr., 1977, 137, 83-91.

R. Bodor, M. Žúborová, E. Ólvecká, V. Madajová, M. Masár, D. Kaninasky, B. Stanislawski, *Isotachophoresis and isotachophoresis-zone electrophoresis of food additives on as chip with column-coupling separation channels*. J. Sep. Sci, 2001, 24, 802-809.

B. J. Davis. *Disc electrophoresis: II. Method and application to human serum proteins*. Ann. N.Y. Acad. Sci. 1964, 121, 404-427.

M. Deml, P. Boček, J. Janák: *High-speed isotachophoresis: current supply and detection system*. J. Chromatogr. A, 1975, 109, 49-55.

V. Dolník, M. Deml and P. Boček: *Multivalent ion interactions in isotachophoresis and their utilization in a cascade system*. In: C. J. Holloway, (Ed.), *Analytical and Preparative Isotachophoresis*, Walter de Gruyter, Berlin-N.Y., 1984, pp. 55-62.

V. Dolnik, M. Deml, P. Boček, *Large sample volume preseparation for trace analysis in isotachophoresis*. J Chromatogr, 1985, 320, 89-97.

V. Dolnik, M. Deml, P. Boček, *Determination of oxalate in human serum by multicolumn isotachophoresis*. Electrophoresis, 1988, 9, 839-841.

V. Dolnik, M. Deml, P. Gebauer, P. Boček, *Optimization of isotachophoretic analysis: use of the charge-based transient state model*. J. Chromatogr., 1991, 55, 249-266.

F. M. Everaerts, Th. P. E. M. Verheggen: *Isotachophoresis: Applications in the biochemical field*. J. Chromatogr. A, 1974, 91, 837-851.

F. M. Everaerts, Th. P. E. M. Verheggen, J. L. M. Van De Venne: *Isotachophoretic experiments with a counter flow of electrolyte*. J. Chromatogr. A, 1976, 123, 1139-148.

F. M. Everaerts, Th. P. E. M. Verheggen, F. E. P. Mikkers, *Determination of substances at low concentrations in complex mixtures by isotachophoresis with column coupling*. J. Chromatogr. A, 1979, 169, 21-38

J. A. Fracassi da Silva and C. L. do Lago: *An Oscillometric Detector for Capillary Electrophoresis*. Anal. Chem., 1998, 70, 4339-4343.

X. C. Huang, M. A. Quesada, R. A. Mathies: *Capillary array electrophoresis using laser-excited confocal fluorescence detection*. Anal. Chem., 1992, 64, 967-972.

J. W. Jorgenson, K. DeArman Lukacs: *Zone electrophoresis in open-tubular glass capillaries*. Anal. Chem., 1981, 53, 1298-1302.

D. Kaniansky, M. Masar, J. Bielcikova, F. Ivanyi, F. Eisenbeiss, B. Stanislawski, B. Grass, A. Neyer, M. Johnck, *Capillary electrophoresis separations on a planar chip with the column-coupling configuration of the separation channels*. Anal Chem. 2000, 72, 3596-3604.

J. Namiesnik *Trace Analysis—Challenges and Problems*. Crit. Rev. Anal. Chem., 2002, 32, 271-300.

D. L. Olson, M. E. Lacey, A. G. Webb, and J. V. Sweedler: *Nanoliter-Volume $^1H$ NMR Detection Using Periodic Stopped-Flow Capillary Electrophoresis*. Anal. Chem., 1999, 71, 3070-3076.

L. Ornstein. *Disc electrophoresis: Background and theory*. Ann. N.Y. Acad. Sci., 1964, 121, 321-349.

P. Pantůčková, M. Urbánek, L. Křivánková, *Determination of iodide on samples with complex matrices by hyphenation of capillary isotahcophoresis and zone electrophoresis*. Electrophoresis, 2007, 28, 3777-3785.

J. C. Reijenga, Th. P. E. M. Verheggen, F. M. Everaerts: *Fluorescence emission and fluorescence quenching as detection methods in isotachophoresis*. J. Chromatogr. A, 1984, 203, 99-111.

R. D. Smith, C. J. Baringa, H. R. Udseth: *Improved electrospray ionization interface for capillary zone electrophoresis-mass spectrometry*. Anal. Chem., 1988, 60, 1948-1952.

J. V. Sweedler, J. B. Shear, H. A. Fishman, R. N. Zare, R. H. Scheller: *Fluorescence detection in capillary zone electrophoresis using a charge-coupled device with time-delayed integration*. Anal. Chem., 1991, 63, 496-502.

J. Tanyanyiwa and P. C. Hauser: *High-voltage contactless conductivity detection of metal ions in capillary electrophoresis*. Electrophoresis, 2002, 23, 3781-3786.

Th. P. E. M. Verheggen, F. M. Everaerts, *Volume-coupling in isotachophoresis*. J. Chromatogr. A, 1982, 249, 221-230.

A. Zemann, E. Schnell, D. Volgger, and G. K. Bonn: *Contactless Conductivity Detection for Capillary Electrophoresis*. Anal. Chem., 1998, 70, 563-567.

FIELD OF THE INVENTION

The present invention relates to electrophoretic separation and analysis of trace and ultra-trace compounds. Specifically the invention is directed to analysis of ionogenic compounds by coupled isotachophoresis and zone electrophoresis on chip with online detection.

BACKGROUND OF THE INVENTION

Trace and Ultra-Trace Analysis

Environmental protection agency defines trace analysis as analysis at part-per-thousand level (http://www.epagov/esd/chemistry/org-anal/faq.htm).

According to IUPAC definition, trace analysis corresponds to analysis of compounds below 100 ppm (<0.01%). Microtrace analysis corresponds to analysis below 1 ppm ($<10^{-4}$%), ultra-microtrace analysis to analysis below 1 ppb ($<10^{-7}$%), and sub-microtrace analysis to analysis below 1 ppt ($<10^{-10}$%) (J. Namiesnik Trace Analysis—Challenges and Problems. Crit. Rev. Anal. Chem. 32, 271-300, 2002).

Separation in Isotachophoresis

In isotachophoresis (ITP), the concentration of ions in their pure isotachophoretic zones, is set up by their mobilities, the mobilities of the used leading ion and counter ion and the concentration of the leading ion and is independent of the original concentration of analytes in the sample. Thus, low-concentration analytes are concentrated between leading ion and terminating ion, which, in combination with a suitable detection method, makes it a useful tool for a rapid ion analysis. To achieve a full isotachophoretic separation of analytes, a certain amount of electric charge has to pass through the separation column (Boček, P., et al., *Analytical isotachophoresis: The concept of the separation capacity*. J. Chromatogr., 1979, 160, 1-9.). When so-called effective mobilities of analytes are known, the separation charge and column charge/hold-up can be calculated (Dolník, V., et al., *Optimization of isotachophoretic analysis: use of the charge-based transient state model*. J. Chromatogr., 1991, 55, 249-266.)

Increasing Separation Performance in Isotachophoresis

Complex mixtures require larger separation charge to achieve full separation of all analytes. Isotachophoretic separation requiring a large separation charge in a narrow capillary would need rather impractically long separation times. Various techniques were introduced to provide high separation charge in short separation time, including hydrodynamic counter flow, volume coupling, column coupling, concentration cascade/step, and multicolumn ITP.

Hydrodynamic counter flow allows performing isotachophoretic separation in relatively short separation column (F. M. Everaerts, Th. P. E .M. Verheggen, J. L. M. Van De Venne: *Isotachophoretic experiments with a counter flow of electrolyte*. J. Chromatogr. A, 1976, 123, 1139-148).

The volume coupling is a method, where the isotachophoretic separation is performed in a wide separation channel and detection in a narrow detection channel. (Th. P. E. M. Verheggen, F. M. Everaerts, *Volume-coupling in isotachophoresis*. J. Chromatogr. A, 1982, 249, 221-230).

The column coupling is a method similar to volume coupling. At the interface between two columns of different width, an auxiliary electrode is connected allowing application of high electric current in the separation step without overheating (F. M. Everaerts, Th. P. E. M. Verheggen, F. E. P. Mikkers, *Determination of substances at low concentrations in complex mixtures by isotachophoresis with column coupling*. J. Chromatogr. A, 1979, 169, 21-38).

The column-coupling method was also applied to separation on chip (R. Bodor, et al., *Isotahophoresis and isotachophoresis-zone electrophoresis of food additives on as chip with column-coupling separation channels*. J. Sep. Sci, 2001, 24, 802-809.)

The concentration cascade/step is a method where separation is performed in a channel with a high-concentration leading electrolyte and detection in a channel with a low-concentration leading electrolyte (Boček, P., et al., *Effect of a concentration cascade of the leading electrolyte on the seperation capacity in isotachophoresis*. J. Chromatogr., 1978, 156, 323-326.).

Concentration step and column coupling can also be combined. This approach brings possible additional advantages such as changing migration order and eliminating major interfering compounds (V. Dolník, M. Deml and P. Boček: *Multivalent ion interactions in isotachophoresis and their utilization in a cascade system*. In: C. J. Holloway, (Ed.), *Analytical and Preparative Isotachophoresis*, Walter de Gruyter, Berlin-N.Y., 1984, pp. 55-62.).

The multicolumn isotachophoresis is a method similar to the column coupling. The separation is performed in a channel with a cross section substantially exceeding the cross-section of the analytical capillary (Dolnik, V., et al., *Large sample volume preseparation for trace analysis in isotachophoresis*. J. Chromatogr, 1985, 320, 89-97, Dolnik, V., et al., *Determination of oxalate in human serum by multicolumn isotachophoresis*. Electrophoresis, 1988, 9, 839-841.). To improve dissipation of generated Joule heat, the separation channel has rectangular cross-section as well as the following tapered channel, in which the profile of isotachophoretic zones is reduced. Only a single auxiliary electrode is connected to the tapered channel. During migration through the tapered channel, the fully separated isotachophoretic zones can be partly mixed and have to be restored by migration through a narrow restoring channel. The system may contain a series of tapered and corresponding restoring channels. The final restoring channel serves also as an analytical channel.

Detection in Capillary Electrophoresis

To detect UV absorbing analytes, UV absorption detection can be applied (J. W. Jorgenson, K. DeArman Lukacs: *Zone electrophoresis in open-tubular glass capillaries*. Anal. Chem., 1981, 53 ,1298-1302, M. T. Ackermans, F. M. Everaerts, J. L. Beckers: *Determination of aminoglycoside antibiotics in pharmaceuticals by capillary zone electrophoresis with indirect UV detection coupled with micellar electrokinetic capillary chromatography*. J. Chromatogr. A, 1992, 606, 228-235.

For a sensitive detection of fluorescent compounds, fluorescence detection has been applied (J. C. Reijenga, Th. P. E. M. Verheggen, F. M. Everaerts: *Fluorescence emission and fluorescence quenching as detection methods in isotachophoresis*. J. Chromatogr. A, 1984, 203, 99-111). Laser induced fluorescence detection further improves the detection sensitivity (J. V. Sweedler, J. B. Shear, H. A. Fishman, Richard N. Zare, R. H. Scheller: *Fluorescence detection in capillary zone electrophoresis using a charge-coupled device with time-delayed integration. Anal. Chem.,* 1991, 63, 496-502, X. C. Huang, M. A. Quesada, R. A. Mathies: *Capillary array electrophoresis using laser-excited confocal fluorescence detection.* Anal. Chem., 1992, 64, 967-972).

Mass spectrometry has been used to detect zones in CZE (R. D. Smith, C. J. Barinaga H. R. Udseth: *Improved electrospray ionization interface for capillary zone electrophoresis-mass spectrometry. Anal. Chem.,* 1988, 60, 1948-1952.)

Nuclear magnetic resonance has been also use for detection of analytes in CZE. (D. L. Olson, M. E. Lacey, A. G.

Webb, and J. V. Sweedler: *Nanoliter-Volume $^1H$ NMR Detection Using Periodic Stopped-Flow Capillary Electrophoresis*. Anal. Chem., 1999, 71, 3070-3076.)

Analytes that do not provide a specific signal can be detected by potential gradient detection (M. Deml, P. Boček, J. Janak: *High-speed isotachophoresis: current supply and detection system*. J. Chromatogr. A, 1975, 109, 49-55) and conductivity detection (F. M. Everaerts, Th. P. E. M. Verheggen: *Isotachophoresis: Applications in the biochemical field*. J. Chromatogr. A, 1974, 91, 837-851). Recently capacitively coupled contactless conductivity detection (C4D) has been applied particularly to CZE (A. Zemann, E. Schnell, D. Volgger, and G. K. Bonn: *Contactless Conductivity Detection for Capillary Electrophoresis*. Anal. Chem., 1998, 70, 563-567, J. A. Fracassi da Silva and C. L. do Lago: *An Oscillometric Detector for Capillary Electrophoresis*. Anal. Chem., 1998, 70, 4339-4343, J. Tanyanyiwa and P. C. Hauser: *High-voltage contactless conductivity detection of metal ions in capillary electrophoresis*. Electrophoresis, 2002, 23, 3781-3786.)

Combining Isotachophoresis and Zone Electrophoresis

It may be advantageous to combine isotachophoresis concentrating analytes with zone electrophoresis and more sensitive detection and quantitation. Disc electrophoresis was, in principle, combination of ITP and zone electrophoresis without online detection (L. Ornstein. *Disc electrophoresis: Background and theory*. Ann. N.Y. Acad. Sci., 1964, 121, 321-349, B. J. Davis. *Disc electrophoresis: II. Method and application to human serum proteins*. Ann. N.Y. Acad. Sci. 1964, 121, 404-427).

In isotachophoresis, quantitative analysis is typically performed by measuring the length of isotachophoretic zones (Boček, P., et al., *Analytical Isotachophoresis*. 1988, Weinheim: VCH Publisher.). This translates into limited detection sensitivity. Thus, a combination of ITP and capillary zone electrophoresis (CZE) has been introduced, where analytes are concentrated and separated by ITP and detected by CZE (PantůčkováP., et al., *Determination of iodide on samples with complex matrices by hyphenation of capillary isotahcophoresis and zone electrophoresis*. Electrophoresis, 2007, 28, 3777-3785.). The ITP-CZE combined analysis was also performed on microchip (Kaniansky D, Masar M, Bielcikova J, Ivanyi F, Eisenbeiss F, Stanislawski B, Grass B, Neyer A, Johnck M. *Capillary electrophoresis separations on a planar chip with the column-coupling configuration of the separation channels*. Anal Chem. 2000 72, 3596-604, 2000).

Coatings to Suppress Electroosmotic Flow

Electroosmotic flow (EOF) is generated when an electric field is applied to electrolyte in a column that exhibits some electric charged on its inner surface. EOF is detrimental to high-resolutions separations and has to be eliminated.

Chiari (U.S. Pat. No. 6,410,668) disclosed copolymers of various derivatives of acrylamide and methacrylamide with glycidyl group containing monomers to form a highly hydrophilic, dynamic coating that suppresses electroosmotic flow.

Madabhushi et al. (U.S. Pat. No. 5,567,292) disclosed copolymersfor coating suppressing EOF, selected from the group consisting of polylactams, such as poly(vinyl pyrrolidone); N,N-disubstituted polyacrylamides; and N-substituted polyacrylamides.

Dolnik (U.S. Pat. No. 7,799,195) disclosed a permanent wall coating made of thermally immobilized galactomannans to eliminate electroosmotic flow.

BRIEF SUMMARY OF THE INVENTION

The present invention is suitable for analysis of trace and ultra-trace ionogenic analytes by isotachophoresis-zone electrophoresis on a chip made from an electrically insulated material. Disclosed is a setup with a series of side channels connecting electrodes to a tapered channel.

DETAILED DESCRIPTION OF THE INVENTION

Figure 1:
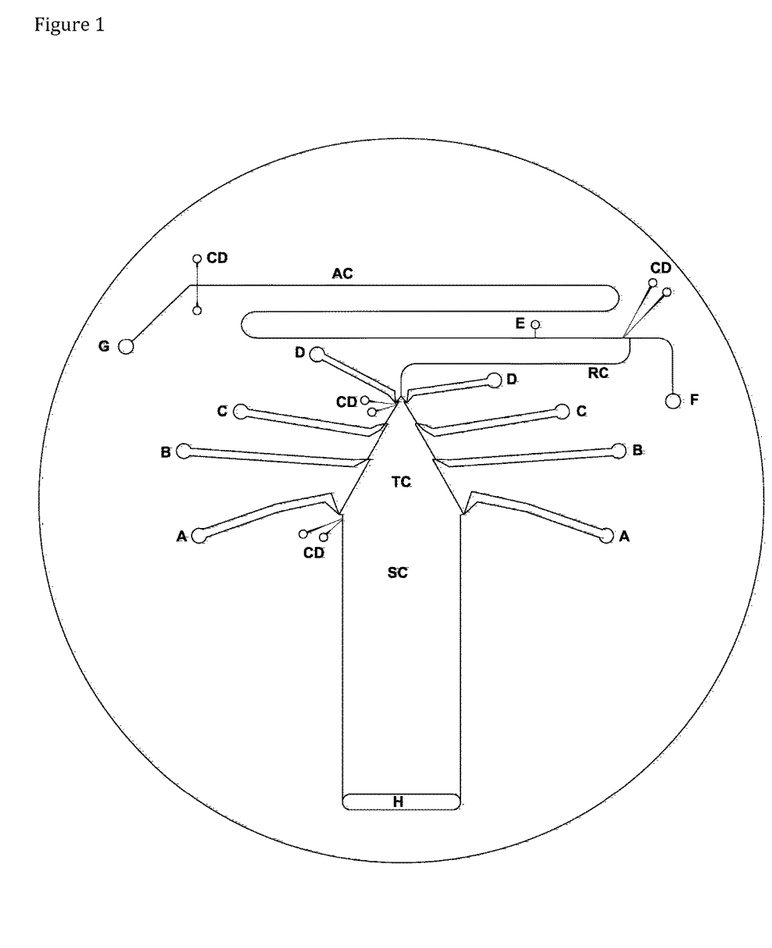
FIG. 1 Microfluidic chip for isotachophoresis—zone electrophoresis. SC—separation channel, TC—tapered channel, RC—restoring capillary channel, AC—analytical capillary channel, A, B, C, D,—leading electrolyte reservoirs, E, F, G—background electrolyte reservoirs, H—terminating electrolyte reservoir, CD—conductivity detector.

We disclose a device for separation and analysis of ionogenic compounds comprising a separation chip, a multichannel power-supply, a detection system, and a system for data acquisition and analysis, where said separation chip comprises a. a separation channel,
b. a tapered channel,
c. at least two side channels connected to said tapered channel,
d. a restoration capillary channel,
e. a side isotachophoretic capillary channel,
f. an analytical capillary channel,
g. a terminating electrolyte reservoir,
h. side leading electrolyte reservoirs connected to said side channels,
i. a leading electrolyte reservoir connected to said side isotachophoretic capillary channel, and
j. at least one background electrolyte reservoir, in the way that said separation channel is connected to said terminating electrolyte reservoir on one side and to said tapered channel on the other side; said tapered channel is connected on its sides to said side channels while said side channels are connected to said side leading electrolyte reservoirs and said tapered channel is connected at its narrow end to said restoration capillary channel; said restoration capillary channel is connected to said analytical capillary channel, when said analytical capillary channel is further connected to said background electrolyte reservoirs, when said analytical capillary channel is also connected via said side isotachophoretic capillary channel to said leading electrolyte reservoir connected to said side isotachophoretic capillary channel.

A device is also disclosed to separate and analyze ionogenic compounds where said separation chip is made from an electrically insulated material selected from group consisting of borofloat glass, fused silica, silicon, poly(methyl methacrylate), polycarbonate, and cyclic polyolefins.

Further we disclose device for separation and analysis of ionogenic compounds, where that comprises an injection device.

We also disclose a device for separation and analysis of ionogenic compounds, where the width of said separation channel is at least forty times larger than the width of said analytical capillary channel.

A device for separation and analysis of ionogenic compounds is also disclosed where said side channels and said tapered channel are interconnected through constrictions of said side channels.

A device for separation and analysis of ionogenic compounds is also disclosed, where said separation channel, said tapered channel, said side channels, said restoration capillary channel, and said analytical capillary channel have a permanent wall coating.

Further we disclose a device for separation and analysis of ionogenic compounds, where at least three pairs of said side channels are connected to said tapered channel when the first pair of said side channels is connected to the end of the separation channel and the beginning of said tapered channel.

We also disclose a device for separation and analysis of ionogenic compounds, where sensing electrodes of a tell-tale detector are connected to said separation channel.

A device for separation and analysis of ionogenic compounds is also disclosed, where sensing electrodes of a tell-tale detector are connected to said tapered channel.

Further we disclose a device for separation and analysis of ionogenic compounds, where the height of said separation channel, said tapered channel, and said analytical capillary channel ranges from about 30 µm to about 100 µm, the width of said separation channel ranges from about 10 mm to about 40 mm. and the width of said analytical capillary channel ranges from about 60 µm to about 200 µm.

We also disclose a device for separation and analysis of ionogenic compounds, where sensing electrodes of a tell-tale detector are connected to said restoration capillary channel.

A method to separate and analyze ionogenic compounds in a microfluidic device is also disclosed, where
  a. prior the analysis, said separation channel, said tapered channel, said side channels, said restoration capillary channel, said side isotachophoretic capillary channel, and said leading electrolyte reservoirs are filled with said leading electrolyte, said terminating electrolyte reservoir is filled with said terminating electrolyte, and said background electrolyte reservoirs and said analytical capillary channel are filled with a liquid;
  b. a sample is loaded;
  c. voltage is applied to electrodes in said leading electrolyte reservoirs and said terminating electrolyte reservoir to perform isotachophoresis of ionogenic analytes in said separation channel;
  d. the presence of isotachophoretic zones of said analytes is detected by said electrodes of said tell-tale detectors;
  e. when the rare boundary of said leading ion is detected at the end of said separation channel, the voltage applied to the electrodes in the first pair of said side leading electrolyte reservoirs is changed to provide electric current of reversed polarity for the time necessary to let said isotachophoretic zones of said analytes migrate just behind the mouth of said side channels, then a voltage is applied to said electrodes in said first pair of said side leading electrolyte reservoirs to turn off said electric current of reversed polarity towards said electrodes in said first pair of said side leading electrolyte reservoirs;
  f. isotachophoretic zones of said analytes migrate further into said tapered channel and the voltage applied to the electrodes in the next pair of said leading electrolyte reservoirs is changed to provide electric current of reversed polarity for the time necessary to let said isotachophoretic zones of said analytes migrate just behind the mouth of said side channels, then a voltage is applied to said electrodes in said pair of said side leading electrolyte reservoirs to turn off said electric current of reversed polarity towards said electrodes in said pair of said side leading electrolyte reservoirs;
  g. when said rear boundary of said leading ion zone is detected by said tell-tale detector at the end of said tapered channel, the voltage is applied to the electrodes in the last pair of said side leading electrolyte reservoirs to provide electric current of reversed polarity for the time necessary to let said isotachophoretic zones of said analytes migrate just behind the mouth of said side channels, then the voltage is applied to said electrodes in said pair of said side leading electrolyte reservoirs to turn off said electric current of reversed polarity towards said electrodes in said pair of said side leading electrolyte reservoirs;
  h. the isotachophoretic zones of said analytes then enter said restoration capillary channel and isotachophoretic boundaries between them, the sharpness of which might have been compromised by previous migration through said tapered channel, are restored by isotachophoretic migration in said restoration channel;
  i. isotachophoretic zones of said analytes are further moved into said analytical capillary channel and further processed.

Further we disclose a method to separate and analyze ionogenic compounds, where said ionogenic compounds are separated and concentrated by isotachophoretic migration in said separation channel at constant current.

We also disclose a device for separation and analysis of ionogenic compounds according to claim 1, also comprising a side zone-electrophoresis capillary channel that is connected to said restoration capillary channel and to a background electrolyte reservoir.

A device for separation and analysis of ionogenic compounds according to claim 3 is also disclosed, where said injection device is a 4-way injection valve.

We disclose a method to separate and analyze ionogenic compounds according to claim 12, where said voltage applied to said electrodes to provide said electric current of reversed polarity is applied for 0-20 s.

A method to separate and analyze ionogenic compounds according to claim 12 is disclosed, where said voltage applied to said electrodes to provide said electric current of reversed polarity is set at the value that generates said electric current of reversed polarity at 0-20% of the absolute value of the original driving current.

We further disclose a method to separate and analyze ionogenic compounds according to claim 12, where, after turning off said electric current of reversed polarity, said voltage is applied to said electrodes to provide electric current of original polarity at 0-20% of the original value.

A method to separate and analyze ionogenic compounds according to claim 12 is also disclosed, where said liquid is said background electrolyte and isotachophoretic zones of said analytes migrate through said analytical capillary channel in zone-electrophoresis mode and said analytes are detected by said analytical detector.

We also disclose a method to separate and analyze ionogenic compounds according to claim 12, where said liquid is said leading electrolyte and isotachophoretic zones of said analyte migrate through said analytical capillary channel in isotachophoretic mode and said analytes are detected by said analytical detector.

We further disclose a device for separation and analysis of ionogenic compounds according to claim 1, where sensing electrodes of an analytical detector are connected to said analytical capillary channel.

EXAMPLES

Example 1

Preparation of Glass Chips

The chip was prepared from borofloat glass wafers 1.1 mm thick with diameter of 10.0 mm. After cleaning the wafers with piranha solution (mixture of 96% sulfuric acid and 30% hydrogen peroxide 9:1) at 120° C. for 20 min, a layer of amorphous silicon was applied in a furnace at 525° C. for 240 min in the presence of $SiH_4$. Then the wafers were coated with hexamethyl disilazane at 110° C. and Shipley photoresist 3612 was applied. A Mylard mask with all the structures drawn on it was used to expose the photoresist layer with UV lamp for 10 s. The exposed photoresist layer was developed and the exposed silicon layer was removed by dry plasma etching in the presence of $SF_6$ and chlorodifluoromethane (F22). Channels were etched with 49% HF at room temperature for 4.5-9 min. Holes of diameter 1.4 mm and 2.0 mm connecting the channels with outer world were drilled with diamond drills on wafers not coated with amorphous silicon. After cleaning all the wafers with piranha solution (mixture of 96% sulfuric acid and 30% hydrogen peroxide 9:1) at 120° C. for 20 min, the upper wafers with drilled holes and lower wafers with etched channels were bonded by anode bonding at 240-300° C. and 1,200 V for 30 min.

Platinum wire with a diameter of 25-75 μm was rolled over with a steel cylinder to make their cross-section elliptic. Then they were inserted into corresponding channels to serve as electrodes for conductivity detection. The sensing electrodes were fixed there by filling the channels with a UV-curable epoxy glue Ultra Light-Weld 3069 (Dymax) and illumination with a UV lamp for 180 s. The electrode reservoirs were attached with the same UV curable epoxy glue.

Example 2

Chip for Isotachophoresis-Zone Electrophoresis

The chip for isotachophoresis-zone electrophoresis on chip contained said separation channel, which was 16 mm wide and 48 mm long. The height of said separation channel as well as the height of all other channels was approx. 45 μm. There was a sampling four-way valve V placed at the beginning of the separation channel, filled with the sample from said sampling inlet S towards said waste outlet W, behind said terminating electrolyte reservoir. In some setups, said sampling valve was eliminated and high-density samples were simply injected at the bottom of said terminating electrolyte. At the end of said separation channel, a pair of sensing electrodes for said tell-tale detector made from 25-75 μm platinum wire were attached. Behind said separation channel, said tapered channel followed, 24 mm long, reducing the cross section from 16 mm to approx. 130 μm. Four pairs of said side channels connected said tapered channel and leading electrolyte reservoirs. The dimensions of said side channels (length 10-25 mm, width 1 mm) were selected not to significantly contribute to resistance of the electric circuit and simultaneously suppress hydrodynamic flow between said electrolyte reservoirs. Constrictions of said side channels at the connection to said tapered channel suppressed loss of analytes by diffusion out of said tapered channel. Said side channels were connected to said tapered channel with an uneven distribution with a shorter distance between them at the narrower part of said tapered channel. At the end of said tapered channel, said restoring channel (130 μm wide, approx. 40 mm long) was connected. Sharp isotachophoretic boundaries that might have been disturbed during their migration through said tapered channel were restored here. Said restoring channel was connected on the other end to said analytical channel (130 μm wide, effective length approx. 150 mm). A pair of sensing electrodes for said tell-tale detector was attached in front of said leading electrolyte reservoir E, i. e., at the end of said restoring channel or at the beginning of said analytical channel. Three electrolyte reservoirs were connected to said analytical channel: said leading electrolyte reservoir via side isotachophoretic capillary channel, said background electrolyte reservoir F via side zone-electrophoretic capillary channel, and said background electrolyte reservoir G. At the end of said analytical capillary channel, a pair of sensing electrodes made from 25-75 μm platinum wire was connected as said analytical detector. A C4D detector was also used in some setups as said analytical detector. In some experiments, said channels were coated with a galactomannan coating (U.S. Pat. No. 7,799,195) to eliminate electroosmotic flow during analysis.

Example 3

Electrolytes Used in the Analysis

Leading Electrolytes LE
1) 50 mM HCl, 100 mM—alanine, 4 g/L hydroxyethyl cellulose (HEC)
2) 50 mM HCl, 100 mM—alanine, 4 g/L hydroxyethyl cellulose (HEC), 50 g/L—cyclodextrin
3) 50 mM HCl, 100 mM—alanine, 50 g/L dextran, $M_w 2 \times 10^6$
4) 50 mM HCl, 150 mM—alanine, 4 g/L hydroxyethyl cellulose (HEC)
5) 50 mM HCl, 150 mM—alanine, 4 g/L hydroxyethyl cellulose (HEC), 50 g/L—cyclodextrin
6) 50 mM HCl, 50 mM—alanine, 50 g/L dextran, $M_w 2 \times 10^6$ Terminating Electrolyte TE
1) 100 mM glycolic acid
2) 100 mM $NaH_2PO_4$
3) 100 mM mandelic acid
4) 20 mM mandelic acid Background Electrolytes BGE
1) 10 mM HCl, 20 mM—alanine, 40 g/L α-cyclodextrin
2) 10 mM HCl, 10 mM—alanine, 40 g/L α-cyclodextrin
3) 10 mM HCl, 20 mM—alanine, 100 g/L poly(vinyl pyrrolidone), $M_w 40,000$
4) 10 mM HCl, 10 mM—alanine, 100 g/L poly(vinyl pyrrolidone), $M_w 40,000$,
5) 10 mM HCl, 20 mM—alanine, 100 g/L poly(vinyl pyrrolidone), $M_w 40,000$, 40 g/L α-cyclodextrin
6) 10 mM HCl, 10 mM—alanine, 100 g/L poly(vinyl pyrrolidone), $M_w 40,000$, 40 g/L α-cyclodextrin

Example 4

Voltage and Current Applied to HVS4448 During Steps 1-Step 6

The analysis by isotachophoresis-zone electrophoresis was typically performed in 6 independent steps. The values for constant current and constant voltage are summarized in Table 1. To speed equilibration of current, initial approximate voltage values were applied at the beginning of a step followed by target constant current values.

TABLE 1

Initial voltage and current values applied

|  | Step 1 | Step 2 | Step 3 | Step 4 | Step 5 | Step 6 |
|---|---|---|---|---|---|---|
| Electrode A | 0 V | 0 μA | 0 μA | 0 μA | 0 μA | 0 μA |
| Electrode B | 600 μA | 600 μA | 0 μA | 0 μA | 0 μA | 0 μA |
| Electrode C | 400 μA | 400 μA | 400 μA | 0 μA | 0 μA | 0 μA |
| Electrode D | 360 μA | 360 μA | 360 μA | 360 μA | 0 μA | 0 μA |
| Electrode E | 60 μA | 0 V | 0 V | 0 V | 0 V | 0 μA |
| Electrode F | 0 μA | 0 μA | 0 μA | 0 μA | 0 μA | −3,000 V |
| Electrode G | 0 μA | 0 μA | 0 μA | 0 μA | 0 μA | 3,000 V |
| Electrode H | −2220 μA | −1500 μA | −900 μA | −420 μA | −80 μA | 0 μA |

Example 5

Performing Isotachophoresis-Zone Electrophoresis on Chip Analysis

First, said analytical capillary channel and said background electrolyte reservoirs were filled with background electrolyte, then said tapered channel, all said side channels, all said leading electrolyte reservoirs, and said separation channel were filled with leading electrolyte. Then said terminating electrolyte reservoir was filled with terminating electrolyte and a sample was applied either with the four-way valve or simply by pipetting it on the bottom of said terminating electrolyte reservoir. When electrodes were connected, a sequence of steps with an 8-channel power supply HVS448 (LabSmith, Inc., Livermore, Calif.) was started. In Step 1, ITP separation was performed. Said tell-tale detector (a contact conductivity detector, Villa Labeco, Spišská Nová Ves, Slovakia) indicated the end of Step 1. Using a comparator LM393P (Texas Instrument, Dallas, Tex.) , a TTL/LTT impuls was sent to the HVS448 and voltages and currents were switched as programmed for Step 2. In Step 2, migration towards electrodes A was disconnected and a low current of 40 μA or less was applied to prevent analytes from entering said side channels connected to said electrodes A. Duration of Step 2, i.e., the time necessary for the colored ITP zone to get in front of said side channels connected to said electrodes B was predetermined with a high-mobility colored marker 2,7-naphthalenedisulfonicacid,4,5-dihydroxy-3-((4-sulfophenyl)azo)-,trisodium (SPADNS). After this time, the sequence switched to Step 3. In Step 3, migration towards electrodes B was stopped and a low current of 40 μA or less was applied on said electrodes B to prevent analytes from entering said side channels connected to said electrodes B. Duration of Step 3 was also predetermined from migration of colored zone of SPADNS. At the end of Step 3, said sequence moved to Step 4 with voltage and current applied as listed in Table 1. Said tell-tale detector (a contact conductivity detector, Villa Labeco, Spišská Nová Ves, Slovakia) indicated the end of Step 4. Using a comparator LM393P (Texas Instrument, Dallas, Tex.), a TTL/LTT impuls was sent to the HVS448 and voltages and currents were switched to progress to Step 5. Said tell-tale detector (a contact conductivity detector, Villa Labeco, Spišská Nová Ves, Slovakia) indicated then the end of Step 5. Using a comparator LM393P (Texas Instrument, Dallas, Tex.), a TTL/LTT impuls was sent to the HVS448 and voltages and currents were switched and Step 6 started. During Step 6, analytes migrated in the zone electrophoretic mode towards the destination electrode in said baground electrolyte reservoir G and their zones were detected by analytical detector, either contact conductivity detector (Villa Labeco, Spišská Nová Ves, Slovakia) or C4D detector (J. A. Fracassi da Silva and C. L. do Lago: *An Oscillometric Detector for Capillary Electrophoresis*. Anal. Chem., 1998, 70, 4339-4343) with wave generator based on the headstage ET121 and C4D detector ER125 (eDAQ, Ltd., Australia).

Example 6

Analysis of Perchlorate in Body Fluids

Figure 2:
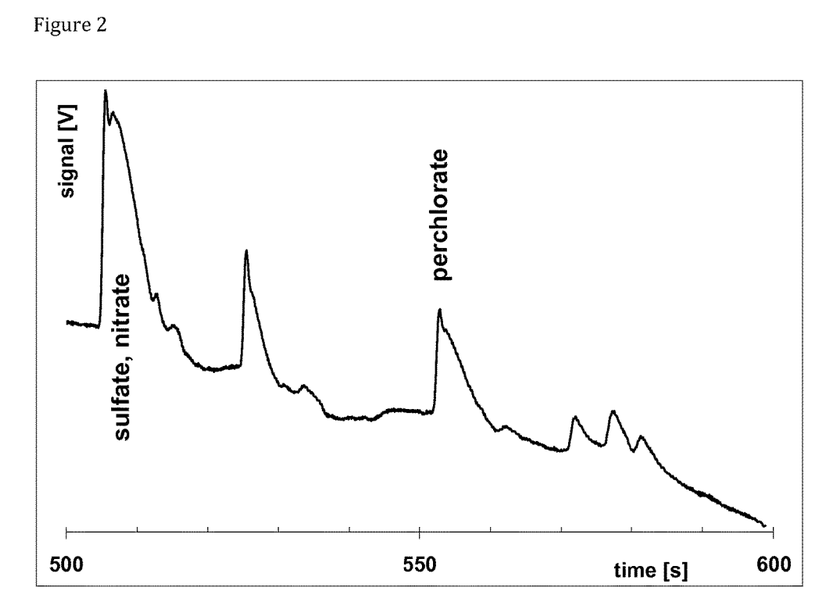
FIG. 2 Analysis of perchlorate in serum ultrafiltrate.
Figure 3:
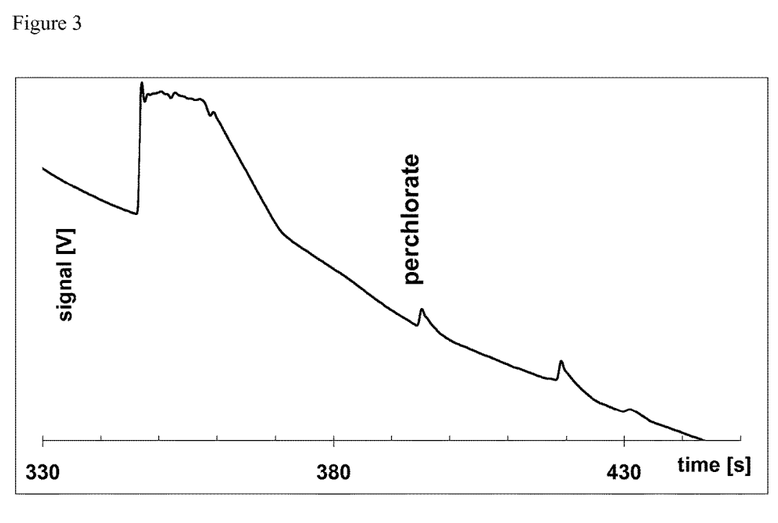
FIG. 3 Analysis of perchlorate in milk ultrafiltrate.

Samples were ultrafiltered through Amicon Ultra centrifugal filters (0.5 mL, 30 k, Millipore) by centrifugation at 14,000 RPM for 30 min. Said capillary channels and said corresponding electrolyte reservoirs (E, F, G) were filled with BGE (10 mM HCl, 10 mM—alanine, 100 mM poly (vinyl pyrrolidone), $M_w$ 40,000), said separation channel, said tapered channel, said side channels and said corresponding leading electrolyte reservoirs (A, B, C, and D) were filled with LE (50 mM HCl, 100 mM—alanine, 50 g/L dextran, Mw 2,000,000), and said terminating electrolyte reservoir (H) with terminating electrolyte (20 mM mandelic acid in 18 MΩ water). 10 μL samples were pipetted on the bottom of said terminating electrolyte reservoir and the analysis was performed according to Example 5.

The invention claimed is:
1. A device for separation and analysis of ionogenic compounds comprising a separation chip, a multichannel power-supply, a detection system, and a system for data acquisition and analysis, where said separation chip comprises
   a. a separation channel,
   b. a tapered channel,
   c. at least two side channels connected to said tapered channel,
   d. a restoration capillary channel,
   e. a side isotachophoretic capillary channel,
   f. an analytical capillary channel,
   g. a terminating electrolyte reservoir,
   h. side leading electrolyte reservoirs connected to said side channels,
   i. a leading electrolyte reservoir connected to said side isotachophoretic capillary channel, and
   j. at least one background electrolyte reservoir,
   where said separation channel is connected to said terminating electrolyte reservoir on a first side and to said tapered channel on a second side that is opposite the first side: said tapered channel is connected on its sides to said side channels while said side channels are connected to said side leading electrolyte reservoirs and said tapered channel is connected at its narrow end to said restoration capillary channel; said restoration cap- illary channel is connected to said analytical capillary channel, said analytical capillary channel is further connected to said background electrolyte reservoir, said analytical capillary channel is also connected via said side isotachophoretic capillary channel to said leading electrolyte reservoir.

2. A device for separation and analysis of ionogenic compounds according to claim 1, where said separation chip is made from an electrically insulated material selected from group consisting of borofloat glass, fused silica, silicon, poly(methyl methacrylate), polycarbonate, and cyclic polyolefins.

3. A device for separation and analysis of ionogenic compounds according to claim 1 further comprising an injection device.

4. A device for separation and analysis of ionogenic compounds according to claim 1, where the width of said separation channel is at least forty times larger than the width of said analytical capillary channel.

5. A device for separation and analysis of ionogenic compounds according to claim 1, where said side channels and said tapered channel are interconnected through constrictions of said side channels.

6. A device for separation and analysis of ionogenic compounds according to claim 1, where said separation channel, said tapered channel, said side channels, said restoration capillary channel, and said analytical capillary channel have a permanent wall coating.

7. A device for separation and analysis of ionogenic compounds according to claim 1, where at least three pairs of said side channels are connected to said tapered channel; the first pair of said side channels is connected to the end of said separation channel and the beginning of said tapered channel.

8. A device for separation and analysis of ionogenic compounds according to claim 1, where sensing electrodes of a tell-tale detector are connected to said separation channel.

9. A device for separation and analysis of ionogenic compounds according to claim 1, where sensing electrodes of a tell-tale detector are connected to said tapered channel.

10. A device for separation and analysis of ionogenic compounds according to claim 1, where the height of said separation channel, said tapered channel, and said analytical capillary channel ranges from about 30 µm to about 100 µm, the width of said separation channel ranges from about 10 mm to about 40 mm, and the width of said analytical capillary channel ranges from about 60 µm to about 200 µm.

11. A device for separation and analysis of ionogenic compounds according to claim 1, where sensing electrodes of a tell-tale detector are connected to said restoration capillary channel.

12. A method to separate and analyze ionogenic compounds in a device according to claim 1, where:
   a. prior to the analysis, said separation channel, said tapered channel, said side channels, said restoration capillary channel, said side isotachophoretic capillary channel, and said leading electrolyte reservoirs are filled with a leading electrolyte, said terminating electrolyte reservoir is filled with a terminating electrolyte, and said background electrolyte reservoirs and said analytical capillary channel are filled with a liquid;
   b. a sample is loaded;
   c. voltage is applied to electrodes in said leading electrolyte reservoirs and said terminating electrolyte reservoir to perform isotachophoresis of ionogenic analytes in said separation channel;
   d. the presence of isotachophoretic zones of said analytes is detected by electrodes of a tell-tale detector;
   e. when a rare boundary of said leading ion is detected at the end of said separation channel, the voltage applied to electrodes in a first pair of said side leading electrolyte reservoirs is changed to provide electric current of reversed polarity for the time necessary to let said isotachophoretic zones of said analytes migrate just behind a mouth of a first pair of side channels then a voltage is applied to the electrodes in said first pair of side leading electrolyte reservoirs to turn off said electric current of reversed polarity towards said electrodes in said first pair of side leading electrolyte reservoirs;
   f. isotachophoretic zones of said analytes migrate further into said tapered channel and the voltage applied to electrodes in a next second pair of side leading electrolyte reservoirs is changed to provide electric current of reversed polarity for the time necessary to let said isotachophoretic zones of said analytes migrate just behind a mouth of a second pair of side channels, then a voltage is applied to said electrodes in said second pair of side leading electrolyte reservoirs to turn off said electric current of reversed polarity towards said electrodes in said second pair of side leading electrolyte reservoirs;
   g. when said rear boundary of said leading ion zone is detected by said tell-tale detector at the end of said tapered channel, the voltage applied to electrodes in a last pair of side leading electrolyte reservoirs is changed to provide electric current of reversed polarity for the time necessary to let said isotachophoretic zones of said analytes migrate just behind a mouth of a last pair of side channels, then the voltage is applied to said electrodes in said last pair of side leading electrolyte reservoirs to turn off said electric current of reversed polarity towards said electrodes in said last pair of side leading electrolyte reservoirs;
   h. the isotachophoretic zones of said analytes then enter said restoration capillary channel and isotachophoretic boundaries between them, the sharpness of which was compromised by previous migration through said tapered channel, are restored by isotachophoretic migration in said restoration channel;
   i. isotachophoretic zones of said analytes are further moved into said analytical capillary channel and further processed.

13. A method to separate and analyze ionogenic compounds according to claim 12, where said ionogenic compounds are separated and concentrated by isotachophoretic migration in said separation channel at constant current.

14. A device for separation and analysis of ionogenic compounds according to claim 1, also comprising a side zone-electrophoresis capillary channel that is connected to said restoration capillary channel and to a background electrolyte reservoir.

15. A device for separation and analysis of ionogenic compounds according to claim 3, where said injection device is a 4-way injection valve.

16. A method to separate and analyze ionogenic compounds according to claim 12, where a modified voltage was applied for 0 to 20 s to provide said electric current of reversed polarity.

17. A method to separate and analyze ionogenic compounds according to claim 12, where said modified voltage to provide said electric current of reversed polarity is set at the value that generates said electric current of reversed polarity at 0-20% of the absolute value of the original driving current.

18. A method to separate and analyze ionogenic compounds according to claim 12, where, after turning off said electric current of reversed polarity, said modified voltage is applied to provide electric current of original polarity at 0-20% of the original value.

19. A method to separate and analyze ionogenic compounds according to claim 12, where said liquid is a background electrolyte and isotachophoretic zones of said analytes migrate through said analytical capillary channel in zone-electrophoresis mode and said analytes are detected by an analytical detector.

20. A method to separate and analyze ionogenic compounds according to claim 12, where said liquid is a leading electrolyte and isotachophoretic zones of said analytes migrate through said analytical capillary channel in isotachophoretic mode and said analytes are detected by an analytical detector.

21. A device for separation and analysis of ionogenic compounds according to claim 1, where sensing electrodes of an analytical detector are connected to said analytical capillary channel.

* * * * *